(12) United States Patent
Altman et al.

(10) Patent No.: US 9,486,213 B2
(45) Date of Patent: Nov. 8, 2016

(54) DRIVE MECHANISM FOR ARTICULATING TACKER

(75) Inventors: Nir Altman, Kibbutz Kfar Etzion (IL); Izhak Fabian, Kfar Truman (IL)

(73) Assignee: THD Lap Ltd., Kfar Truman (IL)

( * ) Notice: Subject to any disclaimer, the term of this patent is extended or adjusted under 35 U.S.C. 154(b) by 633 days.

(21) Appl. No.: 13/295,225

(22) Filed: Nov. 14, 2011

(65) Prior Publication Data

US 2013/0119108 A1    May 16, 2013

(51) Int. Cl.
*A61B 17/068*     (2006.01)
*A61B 17/064*     (2006.01)
*A61B 17/29*      (2006.01)

(52) U.S. Cl.
CPC ...... *A61B 17/068* (2013.01); *A61B 2017/0649* (2013.01); *A61B 2017/2903* (2013.01); *A61B 2017/2908* (2013.01); *A61B 2017/2925* (2013.01); *A61B 2017/2927* (2013.01)

(58) Field of Classification Search
CPC ............ A61B 2017/2905; A61B 2017/00314; A61B 2017/2908; A61B 2017/00323; A61B 2017/0649; A61B 17/068; A61B 2017/2903
USPC ......... 227/175.1, 179.1, 176.1, 901–902, 19; 606/142, 143, 151, 219
See application file for complete search history.

(56) References Cited

U.S. PATENT DOCUMENTS

| | | | |
|---|---|---|---|
| 4,796,607 A * | 1/1989 | Allred et al. | 600/141 |
| 5,810,882 A * | 9/1998 | Bolduc et al. | 606/213 |
| 5,830,221 A * | 11/1998 | Stein et al. | 606/157 |
| 6,685,715 B2 * | 2/2004 | Danitz et al. | 606/157 |
| 6,872,214 B2 * | 3/2005 | Sonnenschein et al. | 606/153 |
| 7,743,960 B2 * | 6/2010 | Whitman et al. | 227/180.1 |
| 8,002,811 B2 * | 8/2011 | Corradi et al. | 606/300 |
| 8,292,933 B2 * | 10/2012 | Zergiebel | 606/305 |
| 2003/0047582 A1 * | 3/2003 | Sonnenschein et al. | 227/176.1 |
| 2005/0171562 A1 * | 8/2005 | Criscuolo et al. | 606/151 |
| 2006/0074407 A1 * | 4/2006 | Padget et al. | 606/1 |
| 2008/0086154 A1 | 4/2008 | Taylor | |
| 2009/0188965 A1 * | 7/2009 | Levin et al. | 227/179.1 |
| 2010/0001038 A1 * | 1/2010 | Levin et al. | 227/179.1 |
| 2010/0133320 A1 * | 6/2010 | Bilotti et al. | 227/176.1 |
| 2010/0270354 A1 * | 10/2010 | Rimer et al. | 227/175.1 |
| 2010/0318107 A1 * | 12/2010 | Mizrahy et al. | 606/151 |
| 2011/0144444 A1 * | 6/2011 | Sakai et al. | 600/206 |
| 2011/0276083 A1 * | 11/2011 | Shelton et al. | 606/205 |
| 2011/0295282 A1 * | 12/2011 | Glick et al. | 606/151 |
| 2012/0160896 A1 * | 6/2012 | Houard | 227/179.1 |

FOREIGN PATENT DOCUMENTS

| EP | 2389873 | 11/2011 |
|---|---|---|
| WO | 2012/158187 | 11/2012 |

OTHER PUBLICATIONS

PCT Written Opinion PCT/US2012/064057, mailed May 8, 2013.

* cited by examiner

*Primary Examiner* — Andrew M Tecco
(74) *Attorney, Agent, or Firm* — Dekel Patent Ltd.; David Klein

(57) ABSTRACT

A tacker for applying a rotary tack, including a drive shaft coupled to a trigger assembly, wherein operating the trigger assembly causes rotation of the drive shaft, a distal portion of the drive shaft passing into an articulated arm that holds rotary tacks, wherein upon operation of the trigger assembly, the drive shaft rotates to cause deployment of the tacks distally out of the articulated arm, and wherein the drive shaft includes a cable on which are located a plurality of axially spaced drive links that transfer rotational motion of the drive shaft to rotation of the tacks.

13 Claims, 6 Drawing Sheets

DRIVE MECHANISM FOR ARTICULATING TACKER

FIELD OF THE INVENTION

The present invention relates generally to devices and methods for applying surgical fasteners, such as rotary tacks, to tissues, such as for hernia repairs and the like, and particularly to an articulating tacker and drive mechanism therefor.

BACKGROUND OF THE INVENTION

A number of surgical, laparoscopic and endoscopic procedures require application of rotary tacks to tissues, such as for hernia repairs and the like.

U.S. patent application Ser. No. 12/166,329 (published number 2010/0001038) to Levin and Altman, the disclosure of which is incorporated herein by reference, describes a tacker for applying such rotary tacks. The tacker includes a drive shaft coupled to a trigger. Operating the trigger causes rotation of the drive shaft. A magazine holds a rotary tack rotatingly connected to the drive shaft. An articulated applicator arm includes a rotatable output shaft and is rotatingly connected to the magazine, which is proximal to the articulated applicator arm. The articulated applicator arm includes one or more pivoting links, each pivoting link including a link shaft. Operation of the trigger causes the driver shaft and the link shafts to rotate so as to distally advance the rotary tack from the magazine past the pivoting links.

Reference is made to FIGS. 1 and 2, which illustrate the articulated applicator arm 40 and tack magazine 41 of the prior art U.S. patent application Ser. No. 12/166,329 (based on FIGS. 4 and 4A of that application). Tack magazine 41 holds rotary tacks 42. Magazine 41 includes a housing 43 in which a drive shaft 44 is journaled. Drive shaft 44 is connected at a proximal end thereof with a drive assembly (not shown), which connects to a trigger assembly (not shown). Upon operation of the trigger assembly, the drive assembly turns drive shaft 44 about its longitudinal axis.

Tack magazine 41 includes a threaded tube 46 disposed at a distal end of driver shaft 44. Tacks 42 are stored in magazine 41 with the coils of tacks 42 being received in the threads of threaded tube 46. Any number of tacks 42 can be stored in magazine 41, such as a dozen or more.

Articulated applicator arm 40 includes pivoting links 47 pivotally connected to one another in series. A housing 52 of each pivoting link 47 includes a link shaft 48 with proximal and distal pivot connections (e.g., pinned connections). For example, the pivoting link 47 closest to tack magazine 41 is pivotally connected to magazine 41 at a pivot connection 49. The next most distal pivoting link 47 is pivotally connected to the previous pivoting link 47 at a pivot connection 50. By means of the pinned connection, when driver shaft 44 turns all the pivoting links 47 turn as well about their respective longitudinal axes.

Each pivoting link 47 includes a threaded tube 51, similar to threaded tube 46, and tacks 42 advance through the pivoting links 47 by means of the coils of tacks 42 being screwed along the threads of adjacent pivoting links 47. The adjacent pivoting links 47 can pivot through an angular range before their adjacent end faces abut against each other to prevent further angular pivoting.

The housing 52 of each pivoting link 47 and the housing 43 of magazine 41 may be formed with a pair of diametrically opposing bores 53 in which pull cables 118 and 126 are disposed. The pull cables 118 and 126 are attached to a trigger assembly (not shown) and are used to manipulate articulated applicator arm 40.

In operation, the user pulls a trigger or other actuating device to cause driver shaft 44 and all the pivoting links 47 to rotate. This distally advances the tacks 42, one-by-one, from magazine 41 through and past each pivoting link 47 until the tack 42 is advanced off the most distal pivoting link 47 and screws into tissue (not shown). The pull cables 118 and 126 are manipulated by the operator of the trigger assembly to pivot articulated applicator arm 40 to any desired angle. Articulated applicator arm 40 can thus be used at a variety of angles, even a straight orientation.

SUMMARY OF THE INVENTION

The present invention seeks to provide improved drive mechanisms for the tacker of U.S. patent application Ser. No. 12/166,329, as is described more in detail hereinbelow. In particular, the present invention seeks to provide simplified and less expensive construction of the link shaft and/or the drive shaft, and of the threaded tube.

There is thus provided in accordance with a non-limiting embodiment of the present invention a tacker for applying a rotary tack, including a drive shaft coupled to a trigger assembly, wherein operating the trigger assembly causes rotation of the drive shaft, a distal portion of the drive shaft passing into an articulated arm that holds rotary tacks, wherein upon operation of the trigger assembly, the drive shaft rotates to cause deployment of the tacks distally out of the articulated arm, and wherein the drive shaft includes a cable on which are located a plurality of axially spaced drive links that transfer rotational motion of the drive shaft to rotation of the tacks.

In accordance with an embodiment of the present invention the drive links are molded onto the cable, or alternatively, joined onto the cable.

In accordance with an embodiment of the present invention the drive links have an exterior contour that matches an interior contour of the tacks. The exterior contour includes cam surfaces that match correspondingly shaped apertures in the interior contour of the tacks.

In accordance with an embodiment of the present invention, the articulated arm includes a plurality of pivoting links formed with thread forms. The pivoting link may include a male pivot connector and a female pivot connector at opposite ends thereof. Each pivoting link may be constructed of two half-links, which attach to one another.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 3:
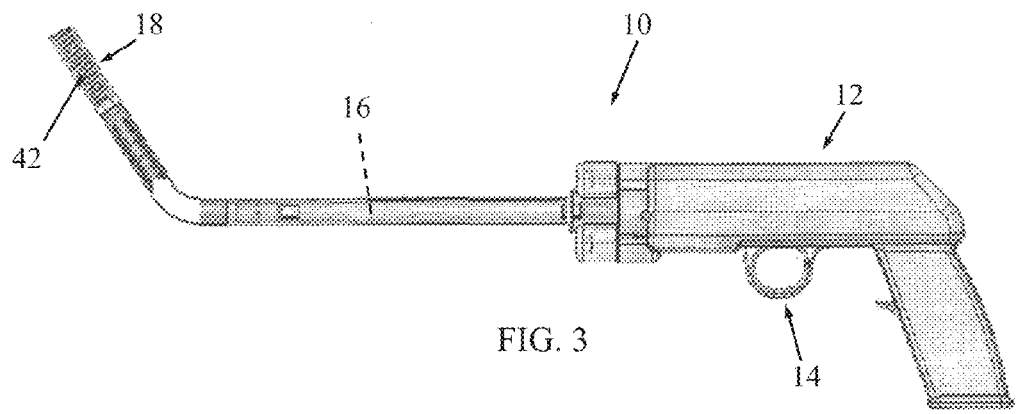
FIG. 3 is a simplified pictorial illustration of a tacker, constructed and operative in accordance with an embodiment of the present invention.

Reference is now made to FIG. 3, which illustrates a tacker 10, constructed and operative in accordance with an embodiment of the present invention.

Figure 1:
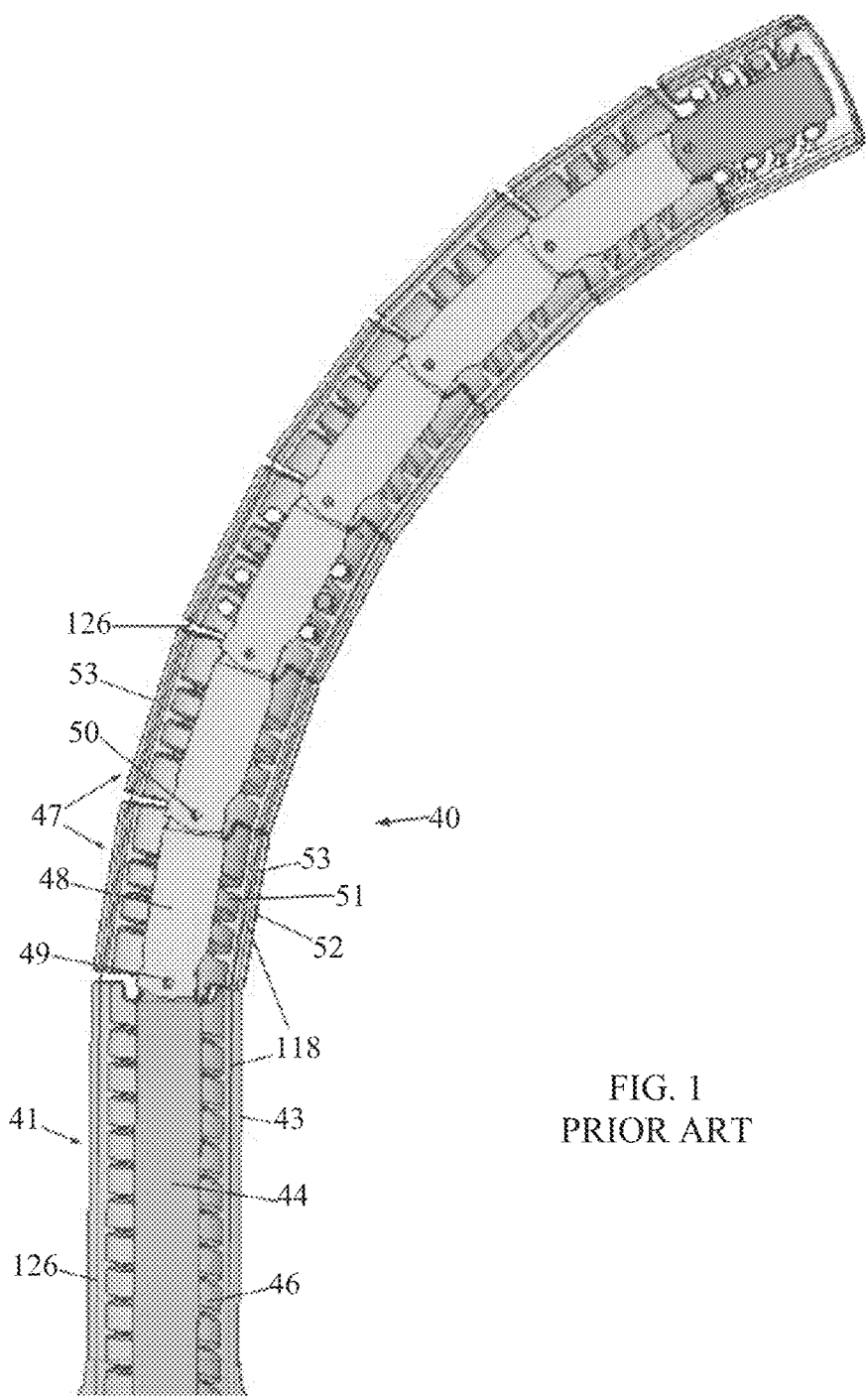
FIGS. 1 and 2 are simplified pictorial illustrations of the drive mechanism of the prior art tacker (U.S. patent application Ser. No. 12/166,329)
Figure 2:
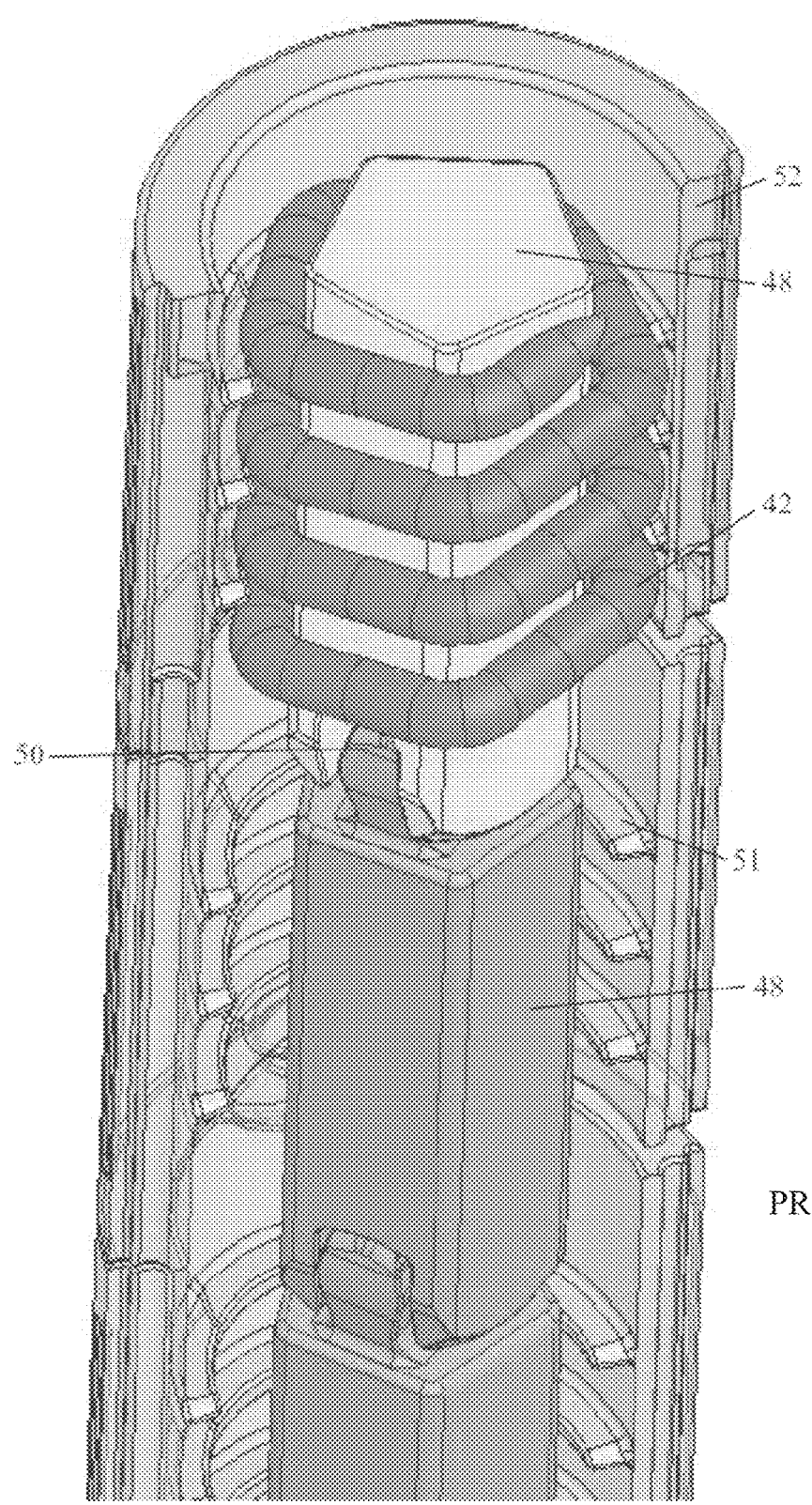

Tacker 10 may include a handle 12 with a trigger assembly 14. A drive shaft 16 is coupled to trigger assembly 14. A distal portion of drive shaft 16 passes into an articulated applicator arm 18, which holds rotary tacks 42 (FIG. 1). As similarly described for the tacker of U.S. patent application Ser. No. 12/166,329, upon operation of trigger assembly 14, the drive assembly turns drive shaft 16 to cause deployment of tacks 42 distally out of articulated applicator arm 18.

Figure 4:
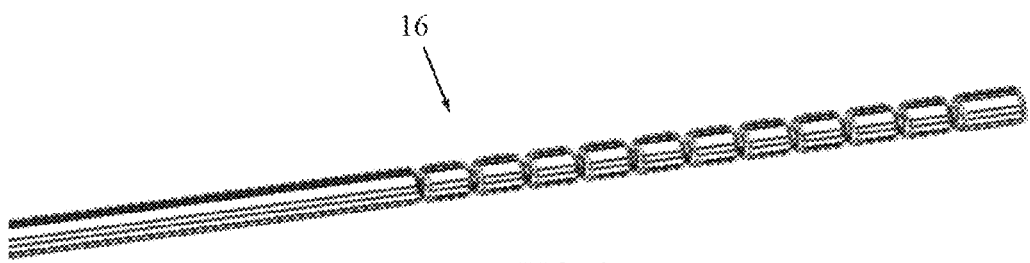
FIGS. 4 and 5 are simplified pictorial and enlarged illustrations, respectively, of a drive shaft or link shaft of the tacker of FIG. 3, constructed and operative in accordance with an embodiment of the present invention.
Figure 5:
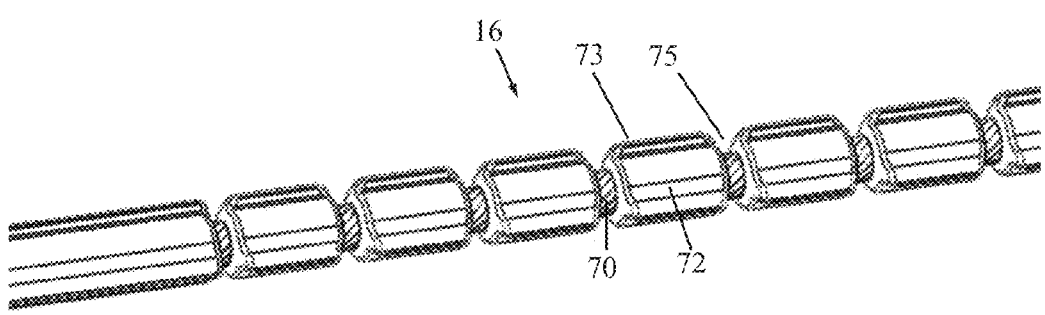
Figure 9:
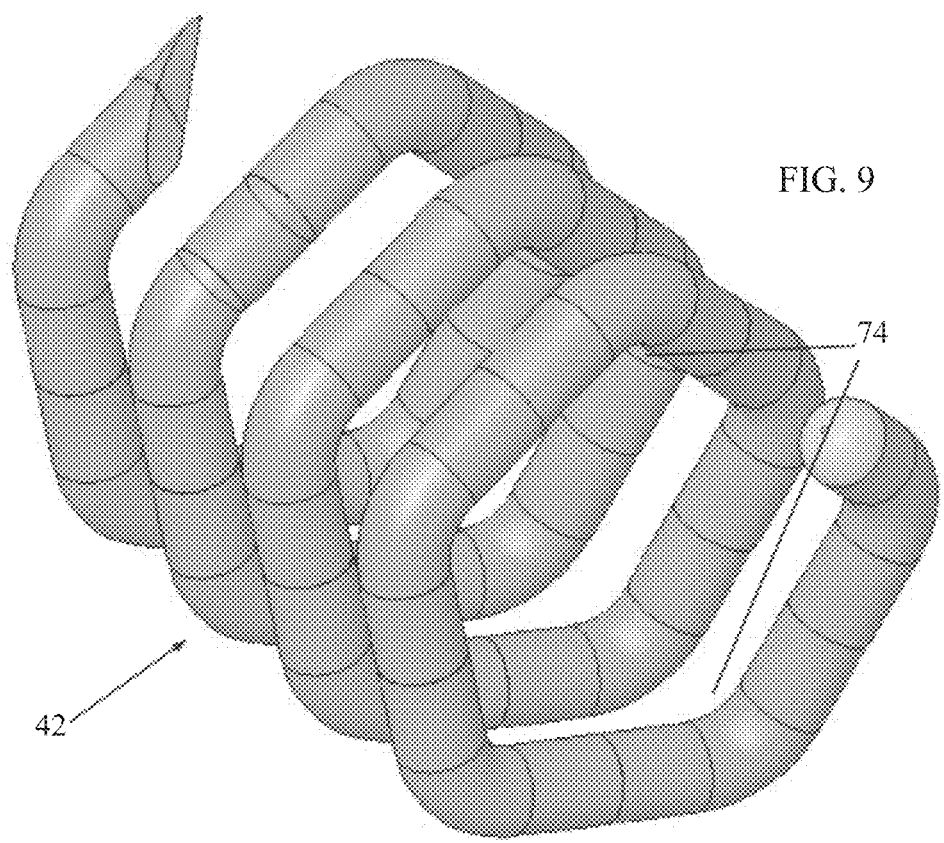
FIG. 9 is a simplified pictorial illustration of a tack, which may be deployed by the tacker of FIG. 3.

Reference is now made to FIGS. 4 and 5, which illustrate a construction of drive shaft 16, in accordance with an embodiment of the present invention. Drive shaft 16 includes a cable 70, made of plastic or metal, on which are located a plurality of axially spaced drive links 72. Drive links 72 may be molded onto cable 70 in an injection molding process (which may be done either for plastic or metal parts). Alternatively, drive links 72 may be joined on cable 70, such as but not limited to, by bonding or welding. Drive links 72 have an exterior contour that matches an interior contour of tacks 42. The exterior contour of drive links 72 is not perfectly round; rather it includes cam surfaces 73 that match correspondingly shaped recesses or apertures 74 in the interior contour of tacks 42 (an example of which is shown in FIG. 9), so that rotation of drive shaft 16 is transmitted via drive links 72 to rotate tacks 42 and advance them eventually off drive shaft 16 into tissue (not shown). Tacks 42 advance as they rotate by virtue of meshing with internal threads of threaded tubes, which are the pivoting links 80 described further below.

In one embodiment, drive shaft 16 is completely rigid. In another embodiment, drive shaft 16 is partially rigid, at its proximal end where it attaches to trigger assembly 14, whereas a distal portion is flexible and bendable. In yet another embodiment, drive shaft 16 is completely flexible and bendable. Where drive shaft 16 is flexible and bendable, gaps 75 between drive links 72 enhance the bending capability of the drive shaft 16. The gaps 75 may be equal. In another embodiment, some of the gaps 75 are different than others. This may impart special bending capability to the drive shaft 16.

Figure 6:
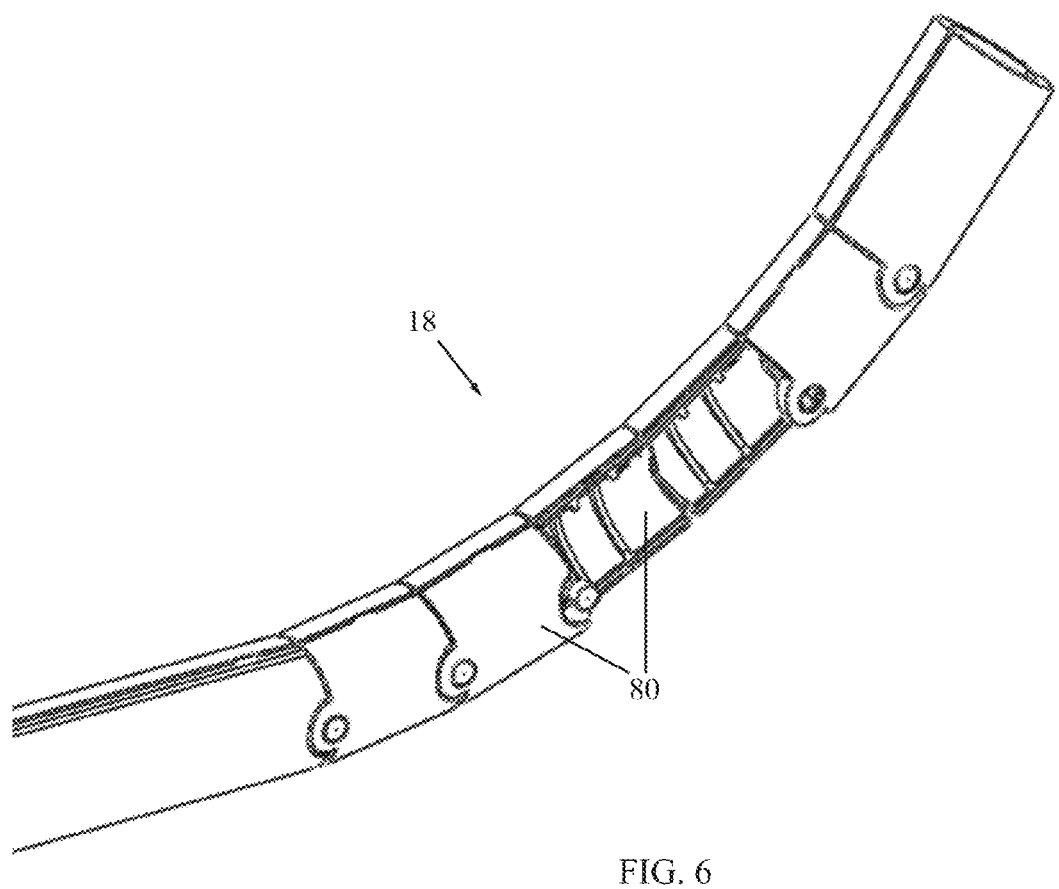
FIG. 6 is a simplified pictorial illustration of an articulated arm of the tacker of FIG. 3, constructed and operative in accordance with an embodiment of the present invention, including a plurality of pivoting links (threaded tubes pivoted to one another)
Figure 7:
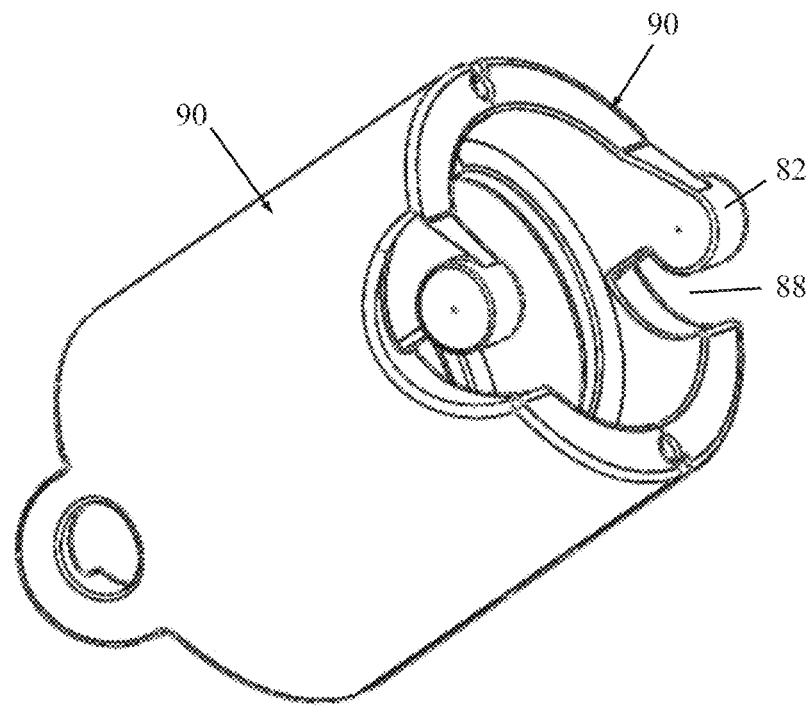
FIGS. 7 and 8 are simplified pictorial illustrations of the pivoting link of the articulated applicator arm.
Figure 8:
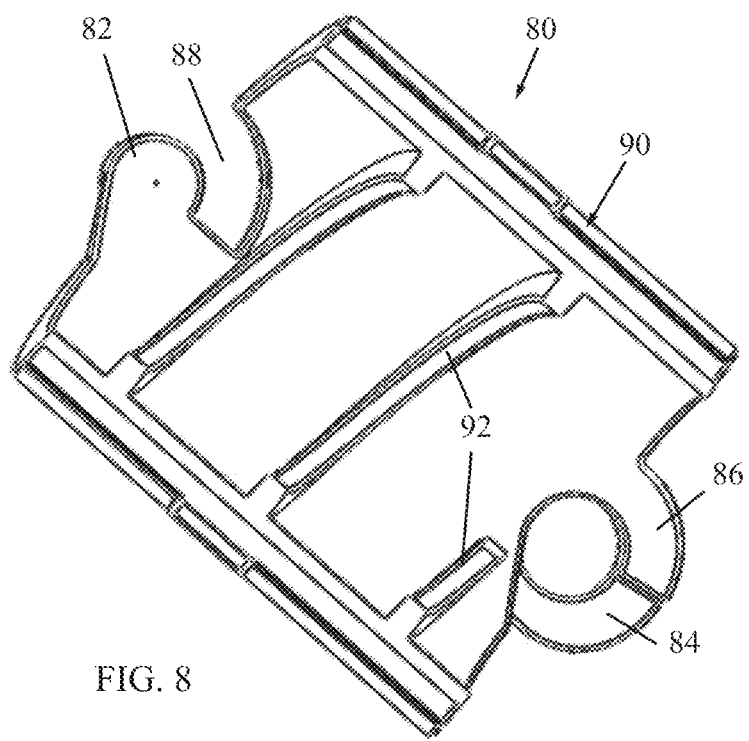

Reference is now made to FIGS. 6-8, which illustrate articulated arm 18 of the tacker of FIG. 3, constructed and operative in accordance with an embodiment of the present invention. Articulated arm 18 includes a plurality of pivoting links 80 (seen best in FIGS. 7-8). In one embodiment of the invention, each pivoting link 80 includes a male pivot connector 82 and a female pivot connector 84 at opposite ends of the link. The male pivot connector 82 is a round lug that swivels in a round hole of the female pivot connector 84. The female pivot connector 84 may be formed with a raised arcuate abutment 86 that fits in an arcuate groove 88 of male pivot connector 82, which serves to limit the pivoting of one link with respect to its neighboring link.

In one embodiment of the invention, each pivoting link 80 is constructed of two half-links 90, which attach to one another, either by snapping together, or by bonding or welding or another suitable process. Each pivoting link 80 is formed with thread forms 92. Accordingly, the pivoting links 80 are threaded tubes pivoted to one another, as seen in FIG. 6. The thread forms may be completely around the inner perimeter or may only be partially around the inner perimeter.

Pivoting links 80 may be made by injection molding of plastic. Alternatively, pivoting links 80 may be made by metal injection molding (MIM), e.g., using a steel alloy, e.g., a stainless steel alloy, such as but not limited to, 17-4PH, a precipitation hardening martensitic stainless steel.

However, even though MIM is preferred for reducing costs and maintaining good manufacturing tolerances, it is recognized that the parts may be made by other methods, such as machining.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. A tacker for applying a rotary tack, comprising:
a drive shaft coupled to a trigger assembly, wherein operating said trigger assembly causes rotation of said drive shaft, a distal portion of said drive shaft passing into an articulated arm that holds rotary tacks, wherein upon operation of said trigger assembly, said drive shaft rotates to cause deployment of said tacks distally out of said articulated arm;
and wherein said drive shaft passes through apertures formed in a plurality of axially spaced drive links, each of the apertures being formed axially through each of the drive links, said drive links operable to transfer rotational motion of said drive shaft to rotation of said tacks.

2. The tacker according to claim 1, wherein said drive links are molded onto said drive shaft.

3. The tacker according to claim 1, wherein said drive links are joined onto said drive shaft.

4. The tacker according to claim 1, wherein said drive links have an exterior contour that matches an interior contour of said tacks.

5. The tacker according to claim 4, wherein said exterior contour comprises cam surfaces that match correspondingly shaped apertures in the interior contour of said tacks.

6. The tacker according to claim 1, wherein said drive shaft is rigid where it attaches to said trigger assembly, whereas a distal portion of said drive shaft is flexible and bendable.

7. The tacker according to claim 1, wherein said articulated arm comprises a plurality of pivoting links formed with thread forms.

8. The tacker according to claim 7, wherein each said pivoting link comprises a male pivot connector and a female pivot connector at opposite ends thereof.

9. The tacker according to claim 7, wherein each said pivoting link is constructed of two half-links, which attach to one another.

10. The tacker according to claim 7, wherein said thread forms are completely around an inner perimeter of said pivoting link.

11. The tacker according to claim 7, wherein said thread forms are partially around an inner perimeter of said pivoting link.

12. The tacker according to claim 7, wherein said pivoting links are made by metal injection molding (MIM).

13. The tacker according to claim 1, wherein said drive shaft is one continuous drive shaft common to all of said drive links.

\* \* \* \* \*